US010251990B2

(12) United States Patent
Wegener et al.

(10) Patent No.: US 10,251,990 B2
(45) Date of Patent: Apr. 9, 2019

(54) SYSTEM AND METHOD FOR PROCESSING, INCUBATING, AND/OR SELECTING BIOLOGICAL CELLS

(71) Applicant: Fenwal, Inc., Lake Zurich, IL (US)

(72) Inventors: Christopher J. Wegener, Libertyville, IL (US); Bret M. Olson, Chicago, IL (US); Alaina Schlinker, Chicago, IL (US); Steven Binninger, Evanston, IL (US); Avnie A. Kadakia, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/498,881

(22) Filed: Apr. 27, 2017

(65) Prior Publication Data

US 2017/0313968 A1 Nov. 2, 2017

Related U.S. Application Data

(60) Provisional application No. 62/329,636, filed on Apr. 29, 2016.

(51) Int. Cl.
*A61M 1/34* (2006.01)
*A61M 1/26* (2006.01)
(Continued)

(52) U.S. Cl.
CPC .......... *A61M 1/3496* (2013.01); *A61M 1/265* (2014.02); *A61M 1/362* (2014.02);
(Continued)

(58) Field of Classification Search
CPC ...... C12M 23/28; C12M 25/02; C12M 27/02; C12M 29/00; C12M 29/04; C12Q 1/24;
(Continued)

(56) References Cited

U.S. PATENT DOCUMENTS

| 5,053,121 A | 10/1991 | Schoendorfer et al. |
| 5,194,145 A | 3/1993 | Schoendorfer |

(Continued)

FOREIGN PATENT DOCUMENTS

| WO | WO 99/34848 | 7/1999 |
| WO | WO 01/45830 | 6/2001 |

(Continued)

OTHER PUBLICATIONS

Wegener et al., U.S. Appl. No. 15/498,965, filed Apr. 27, 2017.
(Continued)

*Primary Examiner* — John Kim
(74) *Attorney, Agent, or Firm* — Cook Alex Ltd.

(57) ABSTRACT

A method for automated processing of a cellular product comprising target substrate cells, the method comprising providing a separation apparatus configured to associate with a disposable sterile circuit comprising a separator in communication with the cellular product. The apparatus and disposable sterile circuit are configured to remove platelets from the cellular product to form a platelet-depleted cellular product, resuspend the platelet-depleted cellular product in media to form a resuspended platelet-depleted cellular product, receive an agent having an association with the target substrate cells of the resuspended platelet-depleted cellular product, incubate the agent with the target substrate cells over a period sufficient for the agent to bind with and/or enter the target substrate cells to form a first mixture comprising agent-target substrate cell complexes, unbound/unassociated agent, and non-target substrate cells, and remove unbound/unassociated agent to form a second mixture comprising the agent-target substrate cell complexes and non-target substrate cells.

10 Claims, 8 Drawing Sheets

(51) Int. Cl.
  *A61M 1/36* (2006.01)
  *C12M 1/00* (2006.01)
  *C12M 1/06* (2006.01)
  *C12M 1/12* (2006.01)
  *C12Q 1/24* (2006.01)
  *G01N 35/00* (2006.01)
  *G01N 35/10* (2006.01)

(52) U.S. Cl.
  CPC ............ *C12M 23/28* (2013.01); *C12M 25/02* (2013.01); *C12M 27/02* (2013.01); *C12M 29/00* (2013.01); *C12M 29/04* (2013.01); *C12Q 1/24* (2013.01); *G01N 35/1016* (2013.01); *G01N 2035/00465* (2013.01)

(58) Field of Classification Search
  CPC ..... G01N 2035/00465; G01N 35/1016; A61M 1/265; A61M 1/362; A61M 1/3496
  See application file for complete search history.

(56) References Cited

U.S. PATENT DOCUMENTS

| | | | |
|---|---|---|---|
| 5,195,145 | A | 3/1993 | Schoendorfer |
| 5,647,985 | A | 7/1997 | Ung-Chhun et al. |
| 5,738,792 | A | 4/1998 | Schoendorfer |
| 5,762,791 | A | 6/1998 | Deniega et al. |
| 5,972,217 | A | 10/1999 | Ung-Chhun et al. |
| 6,143,577 | A | 11/2000 | Bisconte |
| 6,251,284 | B1 | 6/2001 | Bischof et al. |
| 6,251,295 | B1 | 6/2001 | Johnson |
| 6,358,474 | B1 | 3/2002 | Dobler et al. |
| 6,423,023 | B1 | 7/2002 | Chang et al. |
| 6,497,821 | B1 | 12/2002 | Bellamy, Jr. et al. |
| 6,527,957 | B1 | 3/2003 | Deniega et al. |
| 6,706,008 | B2 | 3/2004 | Vishnoi et al. |
| 6,808,503 | B2 | 10/2004 | Farrell et al. |
| 6,863,821 | B2 | 3/2005 | Moriarty et al. |
| 6,960,178 | B2 | 11/2005 | Chang et al. |
| 6,969,367 | B2 | 11/2005 | Tu et al. |
| 6,994,781 | B2 | 2/2006 | Cork et al. |
| 7,364,921 | B1 | 4/2008 | Sciorra et al. |
| 7,390,484 | B2 | 6/2008 | Fraser et al. |
| 7,442,303 | B2 | 10/2008 | Jacobson |
| 7,470,245 | B2 | 12/2008 | Tu et al. |
| 7,514,075 | B2 | 4/2009 | Hedrick et al. |
| 7,585,670 | B2 | 9/2009 | Hedrick et al. |
| 7,771,716 | B2 | 8/2010 | Hedrick et al. |
| 8,105,580 | B2 | 1/2012 | Fraser et al. |
| 8,137,903 | B2 | 3/2012 | Kaufman et al. |
| 8,404,229 | B2 | 3/2013 | Fraser et al. |
| 8,481,336 | B2 | 7/2013 | Earhart et al. |
| 8,637,004 | B2 | 1/2014 | Danilkovich et al. |
| 8,727,132 | B2 | 5/2014 | Miltenyi et al. |
| 8,747,290 | B2 | 6/2014 | Miltenyi et al. |
| 8,808,978 | B2 | 8/2014 | Pages et al. |
| 8,951,782 | B2 | 2/2015 | Chang et al. |
| 9,217,131 | B2 | 12/2015 | Lamish et al. |
| 9,452,254 | B2 | 9/2016 | Kimura et al. |
| 9,511,094 | B2 | 12/2016 | Fraser et al. |
| 9,597,395 | B2 | 3/2017 | Fraser et al. |
| 2005/0048035 | A1 | 3/2005 | Fraser et al. |
| 2005/0048036 | A1 | 3/2005 | Hedrick et al. |
| 2009/0155297 | A1* | 6/2009 | Mrsny ................ A61K 39/385 424/192.1 |
| 2010/0006509 | A1 | 1/2010 | Hornes |
| 2010/0112695 | A1 | 5/2010 | Min |
| 2010/0112696 | A1 | 5/2010 | Min |
| 2012/0055854 | A1 | 3/2012 | Tibbe |
| 2012/0132593 | A1 | 5/2012 | Murthy et al. |
| 2013/0017538 | A1 | 1/2013 | Ionescu-Zanetti et al. |
| 2013/0092630 | A1 | 4/2013 | Wegener |
| 2015/0118728 | A1 | 4/2015 | Rahman et al. |
| 2016/0113967 | A1 | 4/2016 | Hedrick et al. |
| 2016/0244714 | A1 | 8/2016 | Spuhler et al. |
| 2016/0355777 | A1 | 12/2016 | Fachin et al. |
| 2017/0315121 | A1 | 1/2017 | Wegener et al. |
| 2017/0262601 | A1 | 9/2017 | Binninger |
| 2017/0268037 | A1 | 9/2017 | Ionescu-Zanetti et al. |
| 2017/0340783 | A1 | 11/2017 | Wegener et al. |
| 2018/0015418 | A1 | 1/2018 | Binninger et al. |

FOREIGN PATENT DOCUMENTS

| | | |
|---|---|---|
| WO | WO 01/83002 A2 | 11/2001 |
| WO | WO 01/83002 A3 | 11/2001 |
| WO | WO 2012/125457 | 9/2012 |
| WO | WO 2012/125470 | 9/2012 |

OTHER PUBLICATIONS

GE Healthcare Life Sciences, WAVE Bioreactor™ 2/10 system, 6 pages (Aug. 2012).

Hollyman et al., Manufacturing Validation of Biologically Functional T Cells Targeted to CD19 Antigen for Autologous Adoptive Cell Therapy, Journal of Immunotherapy, vol. 32, No. 2, 169-180 (Feb.-Mar. 2009).

Levine et al., Large-Scale Production of CD4 + T Cells from HIV-1-Infected Donors After CD3/CD28 Costimulation, Journal of Hematotherapy 7:437-448 (1998).

ThermoFisher Scientific, DynaMag™ CTS™ Magnet, User Guide, 28 pages (May 25, 2015).

Thompson et al., A Phase I Trial of CD3/CD28-activated T Cells (Xcellerated T Cells) and Interleukin-2 in Patients with Metastatic Renal Cell Carcinoma, Clinical Cancer Research, vol. 9, pp. 3562-3570 (Sep. 1, 2003).

White et al., Intravenous Safety Study in Rats Given Paramagnetic, Polystyrene Beads with Covalently Bound Sheep Anti-Mouse Immunoglobulin G (IgG), Journal of the American College of Toxicology 14(4):251-265 (1995).

European Patent Office, extended European Search Report, counterpart EP Appl. No. 17168424.4, dated Sep. 15, 2017.

* cited by examiner

| | | # of Wash Cycles | Spinner Inlet Flow Rate (mL/min) | Wash Cycle #1 Settings | | | Wash Cycle #2 Settings | | | |
|---|---|---|---|---|---|---|---|---|---|---|
| | | | | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) |
| Settings #1 | Procedure #1 | 2 | 150 | 3750 | 3% | 15 | 150 | 3750 | 3% | 15 |
| | Procedure #2 | 2 | 150 | 3750 | 3% | 15 | 150 | 3750 | 3% | 15 |
| Settings #2 | Procedure #1 | 2 | 80 | 4000 | 6% | 8 | 80 | 4000 | 6% | 8 |
| | Procedure #2 | 2 | 80 | 4000 | 6% | 8 | 80 | 4000 | 6% | 8 |
| Settings #3 | Procedure #1 | 2 | 80 | 4000 | 6% | 8 | 80 | 4000 | 6% | 8 |
| | Procedure #2 | 2 | 148 | 2750 | 7% | 16 | 148 | 2750 | 7% | 16 |

*FIG. 5B*

| Settings #4 | Procedure | # of Wash Cycles | Wash Cycle #1 Settings ||| Wash Cycle #2 Settings ||| Wash Cycle #1 Settings |||
|---|---|---|---|---|---|---|---|---|---|---|---|
| | | | Spinner Inlet Flow Rate (mL/min) | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) | Spinner Inlet Flow Rate (mL/min) | Reduction Spinner Revolution Rate (rpm) | Desired Spinner Inlet PCV | Reduction Retentate Pump Rate (mL/min) |
| | | 3 | 80 | 4000 | 6% | 8 | 80 | 4000 | 6% | 8 | 148 | 2750 | 7% | 16 |

*FIG. 6B*

SYSTEM AND METHOD FOR PROCESSING, INCUBATING, AND/OR SELECTING BIOLOGICAL CELLS

The present application claims the benefit of U.S. Provisional Patent Application No. 62/329,636, filed Apr. 29, 2016, which application is hereby incorporated herein by reference.

FIELD OF THE DISCLOSURE

The present disclosure is directed to processing biological cells. More specifically, the present disclosure relates to methods, systems, and apparatus for washing, processing, incubating, and/or selecting biological fluid using a disposable fluid circuit and a reusable processing apparatus in a sterile system and/or environment.

BACKGROUND

The processing of biological fluid such as blood or blood components typically involves using a reusable processing apparatus ("hardware") and a disposable fluid circuit adapted for mounting or other association with the reusable apparatus. The fluid circuit typically includes containers such as plastic bags and associated tubing that defines a flow path through the circuit. The disposable fluid circuit may also include one or more separation devices by which the biological fluid/cells can be separated into two or more components, washed or otherwise processed. Separation devices may separate the biological fluid based on centrifugal separation and/or membrane separation.

The disposable fluid circuits typically include plastic containers and tubes that are pre-connected, pre-assembled, and pre-sterilized, such as by radiation or steam sterilization. In some processing systems and methods, containers including liquids such as anticoagulant, saline, wash solution, storage media, or treating agents may likewise be pre-attached to the disposable fluid circuit, thereby creating a "closed" system. A "closed" system is one where the interior of the system, i.e., internal flow paths, separation chambers, etc., are not exposed or "opened" to the outside environment.

SUMMARY

According to an exemplary embodiment, the present disclosure is directed to a method for automated processing of a cellular product comprising target substrate cells, in preparation for target cell selection, the method comprising providing a reusable separation apparatus controlled by a microprocessing unit driven by software, said apparatus configurable with a plurality of settings and configured to associate with a disposable sterile circuit comprising a separator comprising a porous membrane and in communication with the cellular product. The apparatus and disposable sterile circuit are configured to remove platelets from the cellular product in a first cycle to form a platelet-depleted cellular product, resuspend the platelet-depleted cellular product in media in a second cycle to form a resuspended platelet-depleted cellular product, receive an agent having an association with the target substrate cells of the resuspended platelet-depleted cellular product, incubate the agent with the target substrate cells over an incubation period sufficient for the agent to bind with and/or enter the target substrate cells to form a first mixture comprising agent-target substrate cell complexes, unbound/unassociated agent, and non-target substrate cells, and remove unbound/unassociated agent in a third cycle to form a second mixture ready for target cell selection. The second mixture comprises the agent-target substrate cell complexes and non-target substrate cells.

According to an exemplary embodiment, the present disclosure is directed to a method for automated processing of a leukapheresis product comprising surface antigen expressing cells, in preparation for surface antigen expressing cell selection, the method comprising providing a reusable separation apparatus controlled by a microprocessing unit driven by software, said apparatus configurable with a plurality of settings and configured to associate with a disposable sterile circuit comprising a separator comprising a porous membrane and in communication with the leukapheresis product. The apparatus and disposable sterile circuit are configured to remove platelets from the leukapheresis product in a first cycle to form a platelet-depleted leukapheresis product, resuspend the platelet-depleted leukapheresis product in media in a second cycle to form a resuspended platelet-depleted leukapheresis product, receive an agent having an association with the surface antigen expressing cells of the resuspended platelet-depleted leukapheresis product, and incubate the agent with the surface antigen expressing cells over an incubation period sufficient for the agent to bind/associate with the surface antigen expressing cells to form a first mixture comprising antigen-agent complexes, unbound/unassociated agent, and cells not presenting the antigen. The apparatus and disposable sterile circuit are also configured to remove unbound/unassociated agent in a third cycle to form a second mixture ready for target cell selection, wherein the second mixture comprises the antigen-agent complexes and cells not presenting the antigen.

According to an exemplary embodiment, the present disclosure is directed to a method for automated processing of a cellular product comprising target substrate cells, in preparation for target cell selection, the method comprising providing a reusable separation apparatus controlled by a microprocessing unit driven by software, said apparatus configurable with a plurality of settings and configured to associate with a disposable sterile circuit comprising a separator comprising a porous membrane and in communication with the cellular product. The apparatus and disposable sterile circuit are configured to remove platelets from the cellular product in a first cycle to form a platelet-depleted cellular product, resuspend the platelet-depleted cellular product in media in a second cycle to form a resuspended platelet-depleted cellular product, receive an agent having an association with the target substrate cells of the resuspended platelet-depleted cellular product, and incubate the agent with the target substrate cells over an incubation period sufficient for the agent to bind with and/or enter the target substrate cells to form a first mixture comprising agent-target substrate cell complexes, unbound/unassociated agent, and non-target substrate cells. The apparatus and disposable sterile circuit are also configured to remove unbound/unassociated agent in a third cycle to form a second mixture ready for target cell selection, wherein the second mixture comprises the agent-target substrate cell complexes and non-target substrate cells.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 5B is a tabular listing of settings to be used in the steps illustrated in FIG. 5A for a reusable hardware apparatus and its controller, according to an exemplary embodiment;

FIG. 6B is a tabular listing of settings to be used in the steps illustrated in FIG. 6A for a reusable hardware apparatus and its controller, according to an exemplary embodiment.

DETAILED DESCRIPTION

There are several aspects of the present subject matter that may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

One or more embodiments described herein may allow for a single system for washing and processing cell products in preparation for target cell selection of those cell products.

Systems and methods for the automated sterile processing of biological fluid are disclosed herein. The systems disclosed may include a reusable separation apparatus and one or more disposable processing circuits adapted for association with the reusable apparatus. The reusable separation apparatus may be any apparatus that can provide for the automated processing of biological fluid. By "automated," it is meant that the apparatus can be pre-programmed to carry out the processing steps of a biological fluid processing method without substantial operator involvement. Even in the automated system of the present disclosure, it should be understood that some operator involvement may be required, such as the loading of the disposable fluid circuits and entering processing parameters. Additional manual steps may be required as well. However, the reusable apparatus may be programmed to process biological fluid through each of the disposable circuits described below without substantial operator intervention.

The reusable processing apparatus may be capable of effecting the separation of a biological fluid that includes biological cells into two or more components or fractions. Thus, the reusable apparatus may generate conditions that allow for the separation of a biological fluid into selected components or fractions. In one embodiment, an apparatus that uses a spinning porous membrane to separate one component from other components may be used for separating biological fluid into its constituent components or fractions. An example of a spinning membrane may be found in U.S. Pat. No. 5,194,145 to Schoendorfer, which is incorporated by reference herein in its entirety, and in International (PCT) Application No, PCT/US2012/028492, filed Mar. 9, 2012, the contents of which are also incorporated herein in its entirety. In addition, systems and methods that utilize a spinning porous membrane are also disclosed in U.S. Provisional Patent Application No. 61/537,856, filed on Sep. 22, 2011, and International (PCT) Application No. PCT/US2012/028522, filed Mar. 9, 2012, the contents of each which are incorporated herein by reference in their entireties. In another embodiment, the reusable apparatus may generate a centrifugal field to effect separation.

Figure 1:
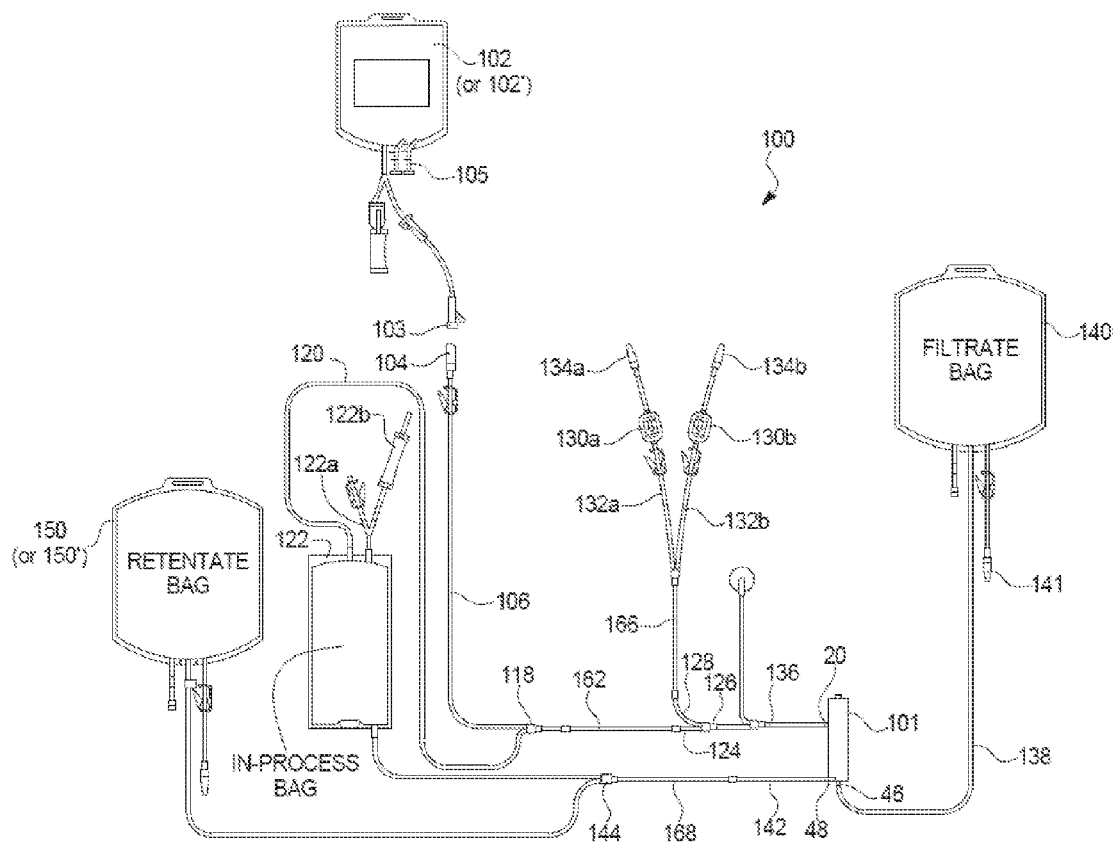
FIG. 1 is a schematic view of a disposable fluid circuit used for processing biological fluid, according to an exemplary embodiment.

Turning now to FIG. 1, a disposable circuit 100 may be used for the separation, washing, volume reduction and/or other processing of a biological fluid. Circuit 100 may include an integrated separation device, such as, but not limited to, a spinning membrane 101 as described above. Circuit 100 may also include waste/filtrate container 140, product/retentate container 150, and in-process container 122. Disposable fluid circuits may further include sampling assemblies (not shown) for collecting samples of source biological fluid, "final" product, or other intermediate products obtained during the biological fluid processing.

Figure 2:
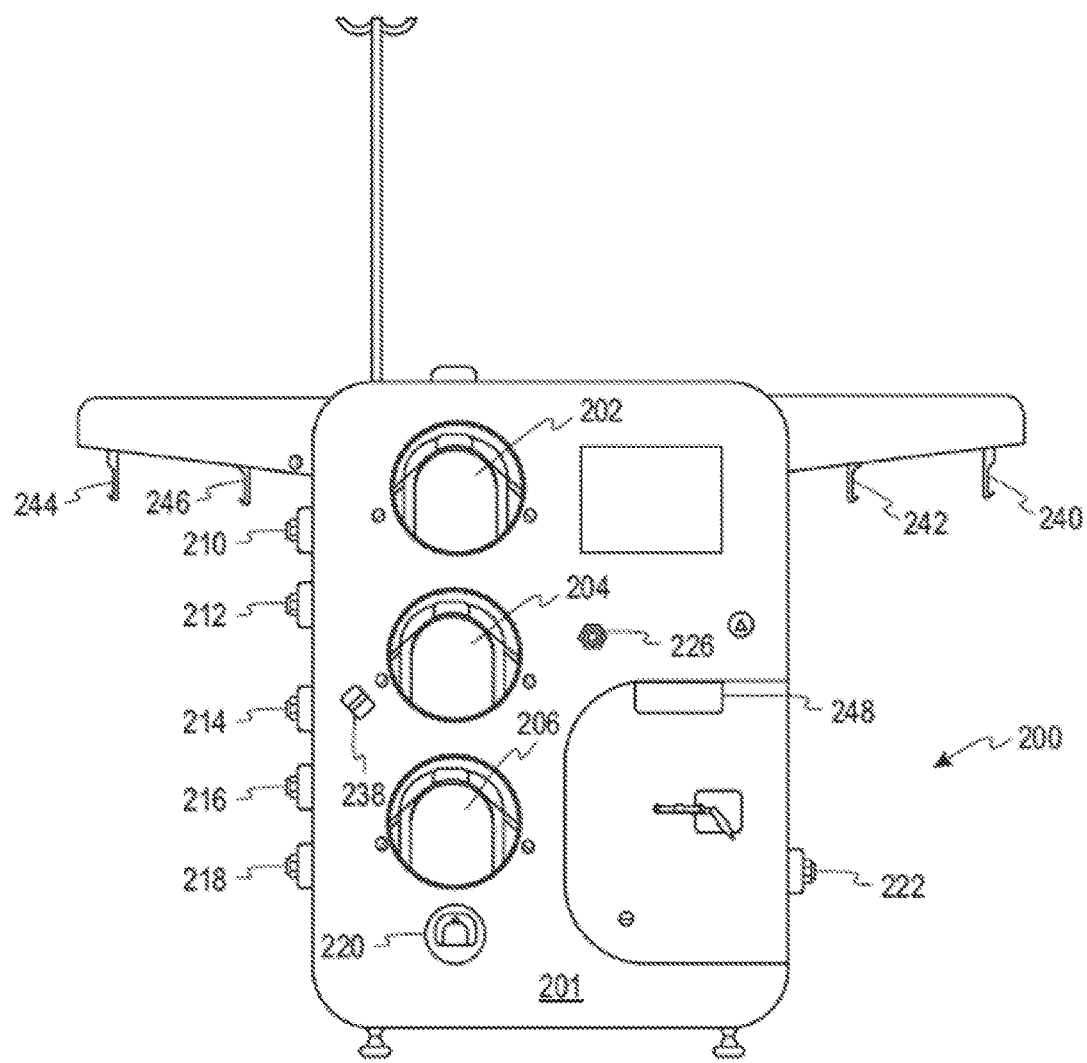
FIG. 2 is an enlarged view of a front panel of a reusable processing apparatus, according to an exemplary embodiment.

Disposable fluid processing circuits may include tubing that defines flow paths throughout the circuits, as well as access sites for sterile and/or other connection to containers of processing solutions, such as wash solutions, treating agents, and/or sources of biological fluid. As shown in FIG. 1, the tubing of circuit 100 may include spaced tubing segments 162, 166, 168. The tubing segments are provided for mating engagement with, e.g., peristaltic pumps of the reusable hardware apparatus 200 (FIG. 2). The containers and the plastic tubing may be made of conventional medical grade plastic that can be sterilized by sterilization techniques commonly used in the medical field, e.g., radiation, autoclaving, etc. Plastic materials useful in the manufacture of containers and of the tubing in the circuits disclosed herein may include plasticized polyvinyl chloride, acrylics, and/or polyolefins.

Source containers may be attached in sterile fashion to the circuit 100. A source container 102 for connection to one disposable circuit may be a product container 150 of another circuit used in a different step of the overall method of processing. Alternatively, the contents of a product container 150 may be further processed or separated and then transferred in sterile fashion to a source container 102 of a later-in-series fluid circuit.

The biological cell suspension to be washed and/or otherwise treated may be provided in a source container 102, shown in FIG. 1. In one embodiment, the source container 102 may initially be disconnected from the disposable set. Source container 102 may have one or ore access sites 103, 105, one of which may be adapted for sterile connection to fluid circuit 100 at docking site 104. Source container 102 may be attached in a sterile manner by employing sterile docking devices, such as CompoDock, available from Fresenius Kabi AG. A second access port 105 may also be provided for extracting fluid from the source container 102 and/or introducing materials into the source container 102.

As shown in FIG. 1, tubing segment 106 extends from docking site 104 and is connected to further downstream branched-connector 118. Branched-connector 118 may communicate with tubing 106 and tubing 120, which may provide a fluid flow path from an "in-process" container 122 described in greater detail below. Tubing segment 124 extends from branched-connector 118 and is joined to a port of further downstream branched-connector 126. A separate flow path defined by tubing 128 may also connect to a port of branched-connector 126.

One or more containers of wash or other processing/treating solution may be attached (or pre-attached) to set 100. Tubings 132a, 132b defining a flow path may include and terminate in an access site such as spike connectors 134a, 134b. Access sites 134a, 134b may establish flow communication with containers 135a, 135b (shown in FIG. 4) of a wash fluid, e.g., saline, additive solution, buffer, etc. Tubings 132a, 132b may include in-line sterile barrier filters 130a, 130b for filtering any particulate from a fluid before it enters the flow path leading to and/or from second branched-connector 126 and, separator 101. The wash media/fluid may flow from the wash fluid source through tubing segments 132a, 132b where it may be filtered by the sterile barrier filters 130a, 130b, and then may pass through tubing 128 to the input of the branched-connector 126.

Tubing segment 136 may define a flow path connected at one end to branched-connector 126 and to an inlet port 20 of the separator 101. As shown in FIG. 1 (and described in greater detail in connection with FIG. 3), the spinning membrane separator 101 may have at least two outlet ports. Outlet 46 of separator 101 may receive waste from the wash (e.g., diluted suspension media) and may be connected to tubing 138, which may define a flow path to filtrate/waste product container 140. The filtrate/waste product container may include a further connection port 141 for sampling or withdrawing the waste from within the waste/filtrate container 140.

Separation device 101 may include a second outlet 48 that is connected to tubing segment 142 for directing desired biological cell/fluid product to a final product/retentate container. The other end of tubing segment 142 may be connected to branched-connector 144, which may branch into and define a flow path to one or more in-process containers 122 and a flow path to the product/retentate container 150.

Turning to FIG. 2, a front panel 201 of a reusable hardware processing apparatus 200 is shown. Apparatus 200 may be of compact size suitable for placement on a table top of a lab bench and adapted for easy transport. Apparatus 200 may also be supported by a pedestal that can be wheeled to a desired location. As shown in FIG. 2, apparatus 200 may include a plurality of peristaltic pumps such as pumps 202, 204 and 206 on front panel 201. Pump segments of the disposable fluid circuit may be selectively associated with peristaltic pumps 202, 204, and 206. The peristaltic pumps may articulate with the fluid set of FIG. 1 at the pump segments identified by reference numerals 162, 166, 168 and advance the cell suspension or other fluid within the disposable set, as will be understood by those of skill in the art. Apparatus 200 may also include clamps 210, 212, 214, 216, 218, 220 and 222. The clamps may be used to control the flow of the cell suspension through different segments of the disposable set.

Apparatus 200 may also include several sensors to measure various conditions. The output of the sensors may be utilized by device 200 to operate one or more wash or processing cycles. One or more pressure transducer sensor(s) 226 may be provided on apparatus 200 and may be associated with a disposable set 100 at certain points to monitor the pressure during a procedure. Pressure transducer 226 may be integrated into an in-line pressure monitoring site (at, e.g., tubing segment 136), to monitor pressure inside separator 101. Air detector sensor 238 may also be associated with the disposable set 100, as necessary. Air detector 238 may be optional and may be provided to detect the location of fluid/air interfaces.

Apparatus 200 may include weight scales 240, 242, 244, and 246 from which the product container 150, in-process container 122, source container 102, and any additional container(s), respectively, may depend and be weighed. The weights of the bags may be monitored by weight sensors and recorded during a washing or other procedure. From measurements of the weight sensors, the device may determine whether a container is empty, partially full, or full and may control the components of apparatus 200, such as the peristaltic pumps 202, 204 and 206 and clamps 210, 212, 214, 216, 218, 220 and 222.

Figure 3:
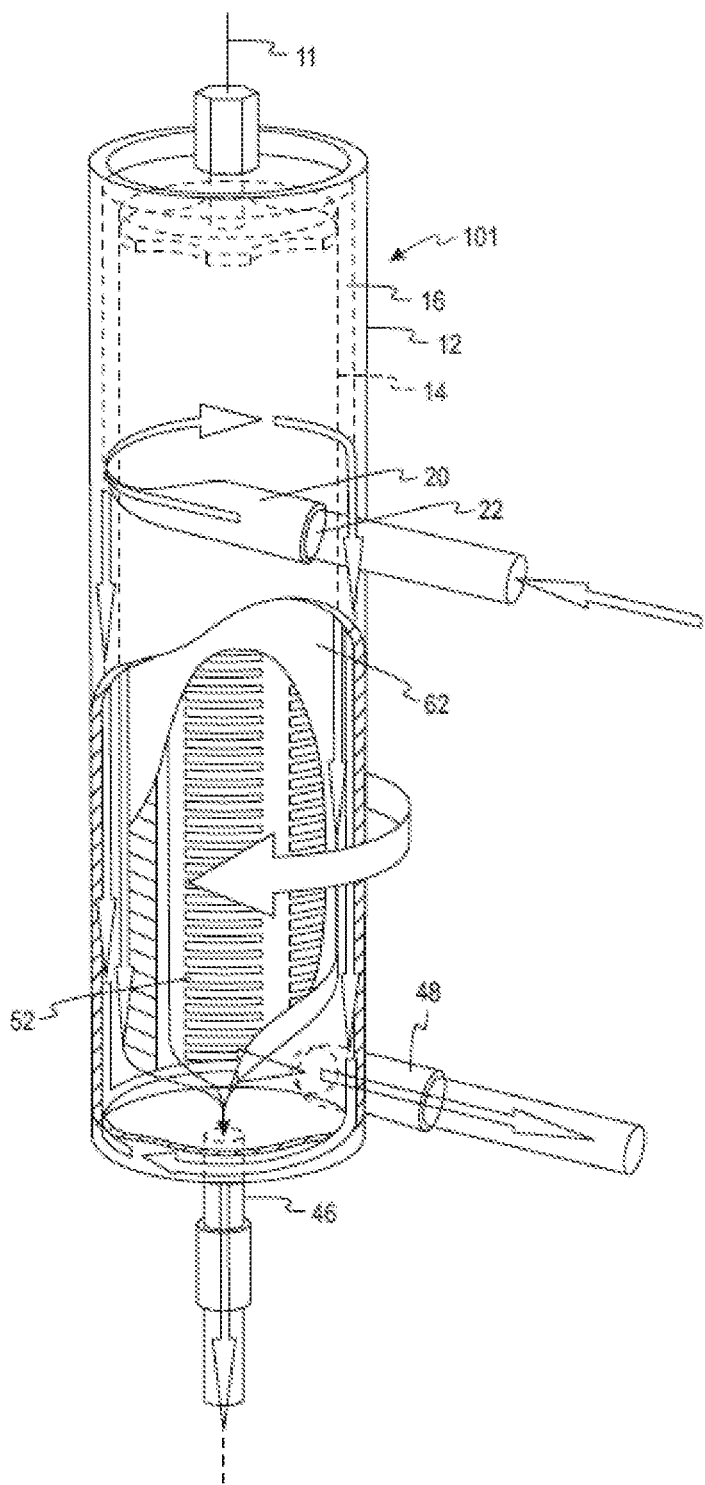
FIG. 3 is a perspective view of a separation/washing device using a spinning membrane, according to an exemplary embodiment.

Apparatus 200 may include a drive unit or "spinner" 248, which may cause the indirect driving of the spinning membrane separator 101. Spinner 248 may consist of a drive motor connected and operated by apparatus 200, coupled to turn an annular magnetic drive member including at least a pair of permanent magnets. As the annular drive member is rotated, magnetic attraction between corresponding magnets within the housing of the spinning membrane separator may cause the spinner within the housing of the spinning membrane separator to rotate. FIG. 3 shows a spinning membrane separator 101 to be in use with the spinner 248. Separator 101 may form part of the disposable circuit 100. Examples and details elating to spinning membrane separators and spinners are disclosed in the aforementioned U.S. Pat. No. 5,194,145, International Application No. PCT/US2012/028492, U.S. Provisional Patent Application No. 61/537,856, and International (PCT) Application No. PCT/US2012/028522, Device 101 may include a generally cylindrical housing 12, mounted concentrically about a longitudinal vertical central axis. An internal member 14 may be mounted concentric with the central axis 11. Housing 12 and internal member 14 may be relatively rotatable. Housing 12 may be stationary and internal member 14 may be a rotating spinner that is rotatable concentrically within cylindrical housing 12, as shown by the thick arrow in FIG. 3. The boundaries of the blood flow path are generally defined by gap 16 between the interior surface of housing 12 and the exterior surface of rotary spinner 14. The spacing between the housing and the spinner is sometimes referred to as the shear gap. In one embodiment, the shear gap may be approximately 0.025-0.050 inches (0.067-0.127 cm) and may be of a uniform dimension along axis 11, for example, where the axis of the spinner and housing are coincident. The shear gap may also vary circumferentially for example, where the axis of the housing and spinner are offset.

The shear gap also may vary along the axial direction, for example, preferably an increasing gap width in the direction. Such a gap width may range from about 0.025 to about 0.075 inches (0.06-0.19 cm). The gap width could be varied by varying the outer diameter of the rotor and/or the inner diameter of the facing housing surface. The gap width could change linearly or stepwise or in some other manner as may be desired. In any event, the width dimension of the gap may be selected so that at the desired relative rotational speed, Taylor Couette flow, such as Taylor vortices, are created in the gap.

Biological fluid may be fed from an inlet conduit 20 through an inlet orifice 22, which directs the fluid into the fluid flow entrance region in a path tangential to the circumference about the upper end of the spinner 14. At the bottom end of the cylindrical housing 12, the housing inner wall includes an exit orifice 48. Cylindrical housing 12 may be completed by a bottom end housing terminating in an outlet orifice 46 concentric with the central axis.

The surface of the rotary spinner 14 may be at least partially, substantially, or entirely, covered by a cylindrical porous membrane 62. The membrane 62 may have a nominal pore size of approximately 4.0 microns, but other pore sizes, for example, of from 0.8 microns to 30.0 microns, may alternatively be used. Membranes useful in the washing methods described herein may be fibrous mesh membranes, cast membranes, track-etched membranes or other types of membranes that will be known to those of skill in the art. For example, in one embodiment, the membrane may have a polyester mesh (substrate) with nylon particles solidified thereon, thereby creating a tortuous path through which only certain sized components will pass. In one embodiment, the nylon membrane may have a pore size of approximately 2.0 µm or less and a thickness of approximately 10 µm or greater. Membranes of this type may retain cellular components (e.g., red blood cells, white blood cells) as well as certain formed blood components, e.g., platelets (~2-4 µm). In another embodiment, the membrane may be made of a thin (approximately 10-50 micron (µm) thick) sheet of, for example, polycarbonate. In this embodiment, pores (holes) may be cylindrical and larger than those described above, e.g., 4.0 µm. The pores may be sized to allow small formed components (e.g., platelets, microparticles, etc.) to pass through, while the desired cells (e.g., white blood cells and larger red blood cells) are collected.

Apparatus 200 and circuit 100 may be used for processing, washing, treating, supernatant exchange, volumetric manipulation, and incubation of biological cells, such as leukocytes, lymphocytes, mononuclear cells, etc., for subsequent therapeutic administration. The steps performed by apparatus 200 may be controlled by a controller, e.g., a microprocessing unit driven by software, with certain steps performed by an operator. For example, the apparatus 200, when switched on, may conduct self-calibration checks, including the checking of the peristaltic pumps, clamps, and sensors. Apparatus 200 may then prompt the user to enter selected procedural parameters, such as the washing procedure to be performed, the amount of cell suspension to be washed, the number of washings to take place, etc. The operator may then select and enter the procedural parameters for the wash procedure.

The microprocessing unit may calculate the volume of wash solution needed for the procedure based on a "maximum output concentration" for the separator, defined as the maximum ratio of the volume of cellular material to the volume of the cell suspension that can be processed by the separator without losing cells of interest. The maximum output concentration may be a function of factors such as the configuration of the membrane, the pore size, and speed of rotation of the membrane. This may be determined or derived empirically for a particular spinner configuration, and pre-programmed into the microprocessor, or a value may be input by the system operator. For purposes of illustration, it will be assumed that the maximum output concentration for the spinning membrane separator is 30% cellular material.

A "concentration ratio," defined as the ratio of the volume of the input to the separator to the output of the separator for the procedure, may be determined. This value may be directly input into the controller by the system operator, or it may be automatically determined by the controller based on other operator input selections. For example, for frozen or thawed cell products, the system may use a concentration ratio of 2:1, while for fresh cell products the concentration ratio used by the system may be 10:1. The input to the separator may be determined by a "spinner inlet flow rate" that may be set by an operator or configured automatically. The output of the separator may be determined by a "reduction retentate pump rate" (also called "spinner outlet flow rate") that may likewise be set by an operator or configured automatically.

A "maximum input concentration," also called "desired inlet spinner packed cell volume (PCV)," may be determined as a function of the maximum output concentration and the concentration ratio, specifically the maximum output concentration divided by the concentration ratio. The desired inlet spinner PCV may indicate the maximum density of cells allowed to enter the separator module to manage the density of cells that exit the spinner. The desired inlet spinner PCV may be set by an operator. During the washing procedure, washing solution may be added to the cells to be washed in an amount so that the cellular concentration of the input to the separator does not exceed the maximum input concentration. By way of example, if the maximum output concentration is 30% and fresh cell products are to be washed, for which the concentration ratio is 10:1, the maximum input concentration is 30%÷10=3%. Thus the volume of wash solution necessary for the procedure should be sufficient to dilute the suspension being input to the separator to a 3% cellular concentration, resulting in an output concentration that does not exceed 30%, and a container 135 containing at least this volume of wash solution should be connected to the disposable set 100 prior to the start of the wash procedure.

A "reduction spinner revolution rate" may be described in revolutions per minute (rpm) and is a measurement of how fast the spinner is spinning. The reduction spinner revolution rate of the spinner may affect how tight the Taylor vortices and how closely target cells reach the membrane. Higher reduction spinner revolution rates may lead to tighter Taylor vortices, leading to decreased mean size of cells retained (not passing through the membrane), and lower reduction spinner revolution rates may allow cells to spread closer to the membrane, leading to increased mean size of cells retained (not passing through the membrane).

EXAMPLES

A. System and Method for Processing Biological Cells and Target Cell Selection

In the following example, the reusable hardware apparatus 200 and its controller may be configured to the following settings, illustrated in FIG. 5B. FIG. 5B sets forth three possible settings for the following system and method. In one embodiment of the system and method, a first and second procedure may be performed, with each procedure comprising two cycles. The settings of apparatus 200 may be such that all cycles of the first and second procedures may comprise a spinner inlet flow rate of 150 mL/min, a reduction spinner revolution rate of 3750 rpm, a desired spinner inlet PCV of 3%, and reduction retentate pump rate of 15 mL/min. In a second embodiment of the system and method, a first and second procedure may be performed, with each procedure comprising two cycles. The settings of apparatus 200 may be such that all cycles of the first and second procedures may comprise a spinner inlet flow rate of 80 mL/min, a reduction spinner revolution rate of 4000 rpm, a desired spinner inlet PCV of 6%, and reduction retentate pump rate of 8 mL/min. In a third embodiment of the system and method, a first and second procedure may be performed, with each procedure comprising two cycles. The settings of apparatus 200 may be such that both cycles of the first procedure comprise a spinner inlet flow rate of 80 mL/min, a reduction spinner revolution rate of 4000 rpm, a desired spinner inlet PCV of 6%, and reduction retentate pump rate of 8 mL/min; and both cycles of the second procedure comprise a spinner inlet flow rate of 148 mL/min, a reduction spinner revolution rate of 2750 rpm, a desired spinner inlet PCV of 7%, and reduction retentate pump rate of 16 mL/min.

Figure 4:
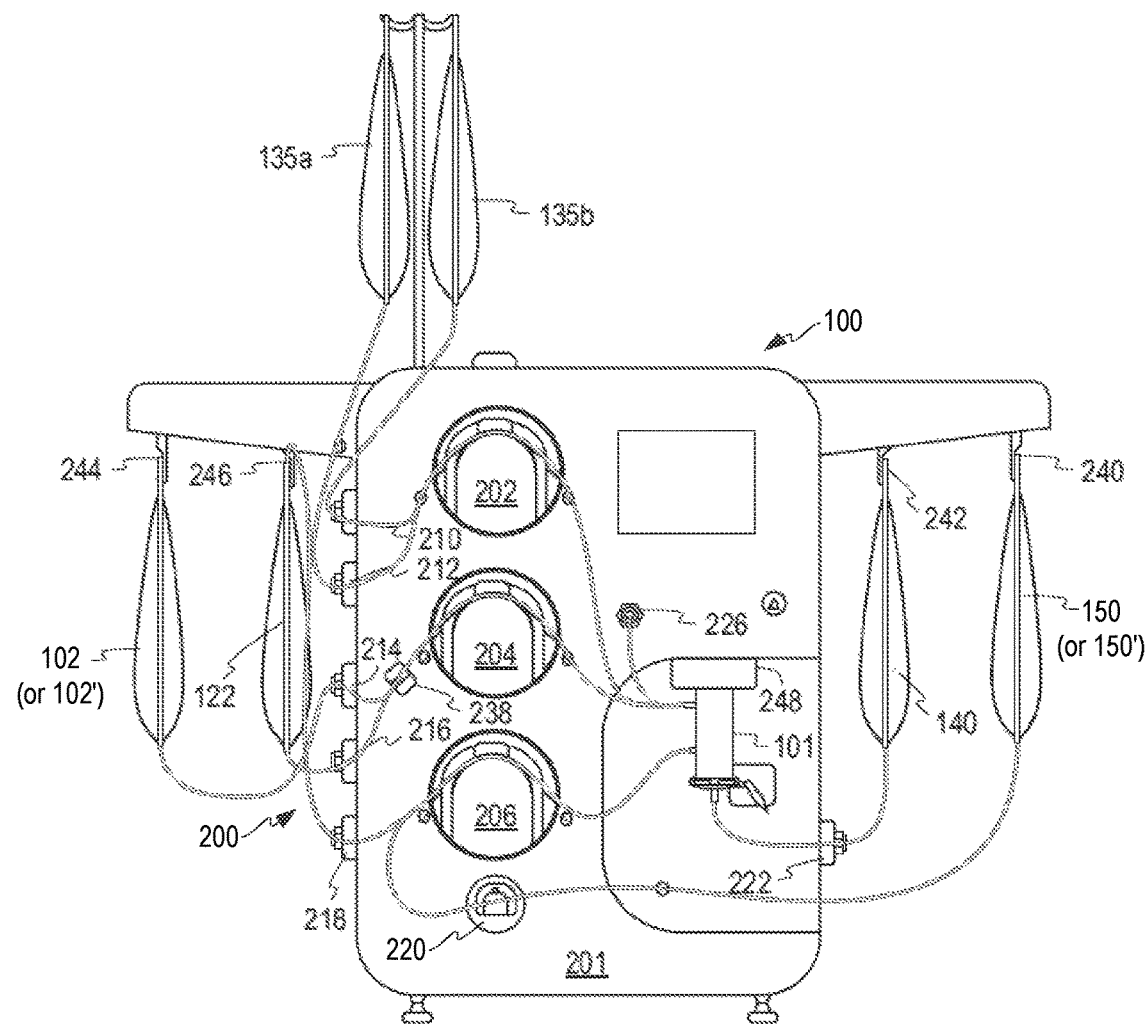
FIG. 4 is a view of the front panel of the reusable processing apparatus of FIG. 2 with the disposable fluid circuit of FIG. 1 loaded thereon, according to an exemplary embodiment.

Referring to FIG. 1 and FIG. 4, in one embodiment, apparatus 200 and circuit 100 may be used to process cell products, e.g., leukapheresis products, in preparation for selection of surface antigen expressing WBCs, e.g., T-cells. A selection system may be used to select specific white blood cells (WBCs), e.g., T-cells. Examples of cell selection systems include fluorescent labeling systems, although any suitable cell selection system may be used.

Figure 5A:
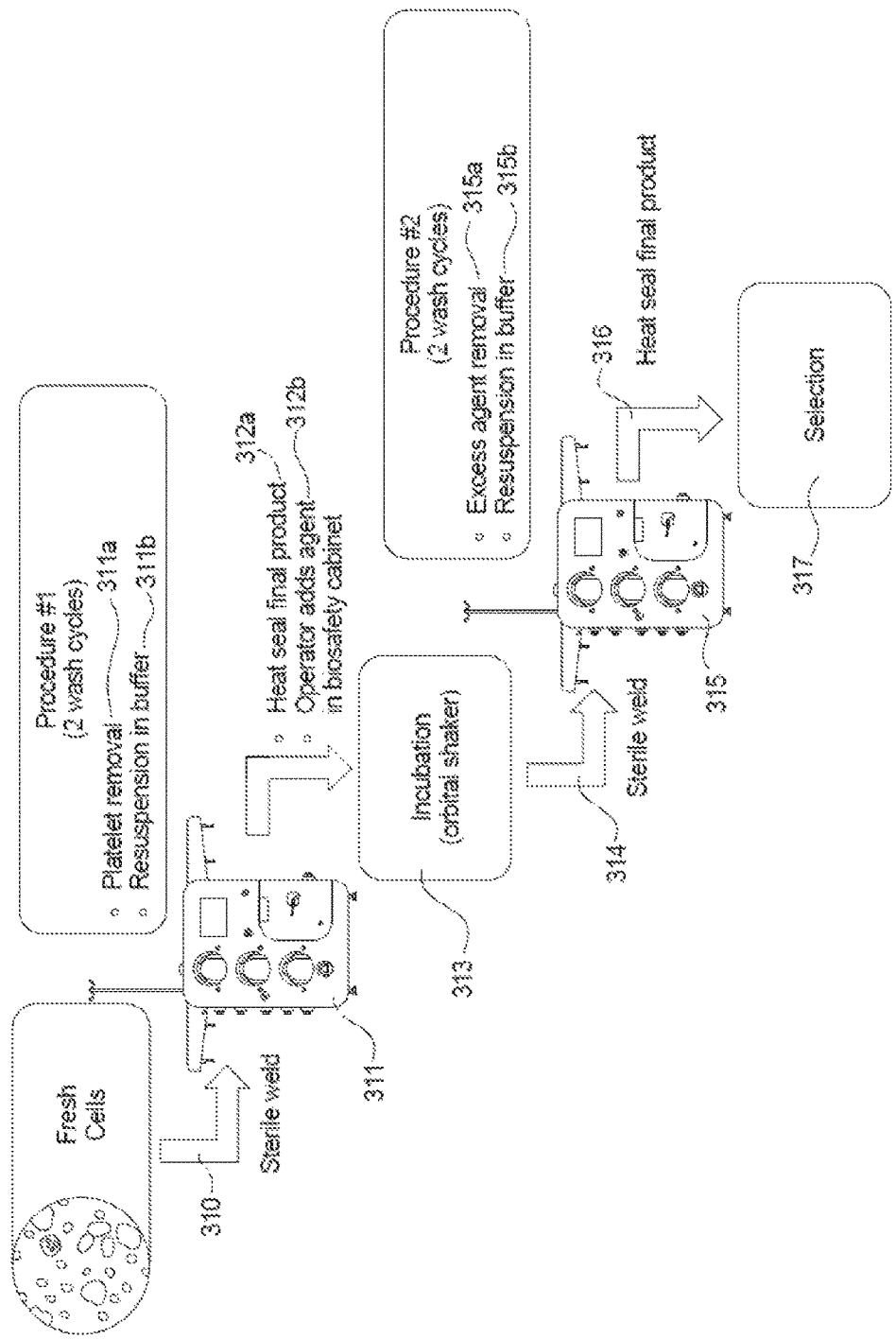
FIG. 5A is a flow diagram illustrating the steps in processing biological cells and performing target cell selection, according to an exemplary embodiment.

Turning to FIG. 5A, a flow diagram is shown, illustrating the steps in processing biological cells and performing target cell selection, according to an exemplary embodiment. At step 310, a sterile circuit 100 may be mounted onto the apparatus 200 (FIG. 4). Source container 102 holding fresh leukapheresis product or any other cell product (e.g., overnight refrigerated, recently obtained via apheresis, etc.) may be sterile-connected to docking site 104 connected to tubing 106. The cell product may comprise leukocytes, e.g., WBCs, T-cells, suspended in a cell additive solution. Also included within the cell product may be platelets and red blood cells suspended alongside the cells. After apparatus 200 determines that the disposable set 100 is properly installed, the controller may prompt the operator to connect a wash medium. Wash container 135a holding the wash medium may be accessed by spike connector 134a of the circuit 100 or sterile welded. The wash medium may comprise a buffer comprising PBS, EDTA, HSA, and/or saline, although any suitable wash medium may be used.

After the source of biological fluid and wash media have been connected to the disposable set, the fluid circuit 100 may commence a first procedure at step 311 comprising supernatant removal and resuspension. The fluid circuit 100 may first be primed for the wash process. The circuit 100 may be primed with the wash medium in container 135a or be primed with saline or any other bio-compatible aqueous solution in container 135b, The controller of apparatus 200 may then commence a first cycle comprising a wash. At step 311a, the cell product in container 102 to be washed may be transferred from source container 102 to the spinning membrane separator 101 via the operation of one or more peristaltic pumps 202, 204 and 206. At approximately the same time, the wash medium in container 135a may be delivered through the circuit 100 to the separator 101. The separator 101 may separate the cell product into target cells, e.g., target leukocytes, and remaining supernatant. The membrane of the separator 101 may be made of a thin (approximately 10-50 micron thick) sheet of, for example, polycarbonate, and have pore sizes of approximately 4 microns, or a suitable pore size allowing platelets to pass through but not target cells, e.g., target leukocytes. The target cells may exit the separator 101 through outlet orifice 48 and be directed to the in-process container 122, while the supernatant and formed elements, e.g., platelets, may exit the separator 101 through outlet orifice 46 and be directed to the waste/filtrate bag 140. The supernatant collected in waste/filtrate bag 140 may comprise the cell additive solution and platelets. Wash medium, e.g., buffer comprising PBS, EDTA, HSA, and/or saline, contained in wash container 135a, may then be pumped through the separator 101 to recover any target cells and/or supernatant remaining in the circuit 100 and respectively direct them to the in-process container 122 and/or waste/filtrate bag 140. The contents of the in-process container 122 may comprise concentrated target cells, e.g., target WBCs, suspended in wash media and red blood cells. In one embodiment, an operator may manually mix the target cells suspended in wash media in the in-process container 122 by holding container 122 with both hands and mixing thoroughly by using a gentle rotating motion, although any suitable mixing method may be used.

At step 311b of FIG. 5A, a second cycle of the first procedure may commence, wherein the contents of the in-process container 122 may be diluted further with wash medium in container 135a or 135b in preparation for another pass through the separator 101. The diluted target cells suspended in wash media in container 122 to be washed and concentrated may be transferred from source container 122 to the spinning membrane separator 101 via the operation of one or more peristaltic pumps 202, 204 and 206. The separator 101 may separate the diluted target cells suspended in wash media into target cells and remaining supernatant. The target cells may exit the separator 101 through outlet orifice 48 and be directed to the product/retentate container 150, while the supernatant may exit the separator 101 through outlet orifice 46 and be directed to the waste/filtrate bag 140. The supernatant collected in waste/filtrate bag 140 may comprise cell additive solution, wash media, platelets, and red blood cells. Wash media, e.g., buffer comprising PBS, EDTA, HSA, and/or saline, contained in wash container 135a or 135b, may then be pumped through the separator 101 to rinse any target cells and/or supernatant remaining in the circuit 100 and respectively direct them to the product/retentate container 150 and/or waste/filtrate bag 140. The contents of the product/retentate container 150 may comprise concentrated target cells suspended in wash media.

After completion of the first procedure, the product/retentate container 150 may be disconnected at step 312a of FIG. 5A from the remainder of the circuit 100 in a sterile manner, e.g., heat-seal. At step 312b, an operator may inject an agent into the product/retentate container 150 within an enclosed, ventilated laboratory workspace, such as a biosafety cabinet. The agent may have a diameter (largest cross-sectional length) of approximately 50 nm, or any suitable diameter smaller than the pore size of the membrane of the separator 101. At step 313, the agent may be incubated with the target cells within the product/retentate container 150 for a suitable period of time, e.g., thirty minutes, on an orbital shaker at a suitable temperature, e.g., room temperature.

A fresh disposable circuit or the previously used circuit 100 at step 310 may be mounted onto the apparatus 200 (FIG. 4). The product/retentate container 150 containing the product comprising target cells incubated with the agent may now serve as source container 102'. At step 314 of FIG. 5A, source container 102' may be sterile-connected to docking site 104 connected to tubing 106. The incubated target cell product may comprise leukocytes, e.g., T-cells bound and/or associated with an agent, T-cells not bound and/or associated with an agent, agent not bound to any cells, and wash media. After apparatus 200 determines that the disposable set 100 is properly installed, the controller may prompt the operator to connect a wash medium. Wash container 135a or 135b holding the wash medium may be accessed by spike connector 134*a* or 134*b* of the circuit 100. The wash medium may comprise a buffer comprising PBS, EDTA, HSA, and/or saline, although any suitable wash medium may be used.

After the source container 102' and wash media have been connected to the disposable set, the fluid circuit 100 may commence a second procedure at step 315 comprising excess agent removal and resuspension. The fluid circuit 100 may be primed for the wash process. The circuit 100 may be primed with the wash medium in container 135*a* or 135*b*, The controller of apparatus 200 may then commence a first cycle comprising a wash. At step 315*a,* the incubated target cell product in container 102' to be washed may be transferred from source container 102' to the spinning membrane separator 101 via the operation of one or more peristaltic pumps 202, 204 and 206. At approximately the same time, the wash medium in container 135*a* or 135*b* may be delivered through the circuit 100 to the separator 101. The separator 101 may separate the incubated target cell product into incubated target cells and remaining supernatant. The membrane of the separator 101 may have pores having sizes greater than the diameter of unbound agent and any remaining platelets but less than the diameter of certain cellular components. In one embodiment in which the cellular components have a diameter of approximately 10 microns, the agent has a diameter of approximately 50 nm, and platelets have a diameter of approximately 3 microns, the pores should have sizes greater than 3 microns and less than 10 microns, thereby allowing unbound agent and any remaining platelets to pass through, while not allowing the target cellular components and target cellular components bound to the agent to pass through. The incubated target cells may exit the separator 101 through outlet orifice 48 and be directed to the in-process container 122, while the supernatant may exit the separator 101 through outlet orifice 46 and be directed to the waste/filtrate bag 140. The supernatant collected in waste/filtrate bag 140 may comprise wash media, any remaining platelets, and unbound agent. Additional wash media, e.g., buffer comprising PBS, EDTA, HSA, and/or saline, contained in wash container 135*a* or 135*b,* may then be pumped through the separator 101 to recover any incubated target cells and/or supernatant remaining in the circuit 100 and respectively direct them to the in-process container 122 and/or waste/filtrate bag 140. The contents of the in-process container 122 containing incubated target cells may comprise, e.g., T-cells bound to agent, T-cells not bound to agent, red blood cells, and wash media. In one embodiment, an operator may manually mix the incubated target cells suspended in wash media in the in-process container 122 by holding container 122 with both hands and mixing thoroughly by using a gentle rotating motion, although any suitable mixing method may be used.

At step 315*b* of FIG. 5A, a second cycle of the second procedure may commence, wherein the contents of the in-process container 122 may be resuspended with wash medium in container 135*a* or 135*b* in preparation for another pass through the separator 101. The incubated target cells resuspended in wash media in container 122 may be transferred from source container 122 to the spinning membrane separator 101 via the operation of one or more peristaltic pumps 202, 204 and 206. The separator 101 may separate the incubated target cells suspended in wash media into incubated target cells and remaining supernatant. The incubated target cells may exit the separator 101 through outlet orifice 48 and be directed to a fresh product/retentate container 150', while the supernatant may exit the separator 101 through outlet orifice 46 and be directed to the waste/filtrate bag 140. The supernatant collected in waste/filtrate bag 140 may comprise wash media, any remaining platelets, and unbound agent. Wash media, e.g., buffer comprising PBS, EDTA, HSA, and/or saline, contained in wash container 135*a* or 135*b,* may then be pumped through the separator 101 to rinse any incubated target cells and/or supernatant remaining in the circuit 100 and respectively direct them to the product/retentate container 150' and/or waste/filtrate bag 140. The contents of the product/retentate container 150' may comprise T-cells bound to agent and T-cells not bound to agent suspended in wash media.

After completion of the second procedure, the product/retentate container 150' may be disconnected at step 316 of FIG. 5A from the remainder of the circuit 100 and from the apparatus 200 in a sterile manner, heat-seal. At step 317, an operator may subject the incubated target cells within container 150' to a cell selection system to separate, e.g., the T-cells bound to the agent from the T-cells not bound to the agent. The unbound T-cells and the agent bound to the T-cells may be subject to a selection process, wherein only the agent bound to the T-cells may be retained, while the unbound/unassociated T-cells may pass through the selection process, thereby effecting separation of the desired T-cells and the undesired T-cells.

B. Abbreviated System and Method for Processing Biological Cells and Target Cell Selection In the following example, the reusable hardware apparatus 200 and its controller may be configured to the following settings, illustrated in FIG. 6B. FIG. 6B sets forth settings for the following system and method. In one embodiment of the system and method, a single procedure may be performed, the single procedure comprising three cycles. The settings of apparatus 200 may be such that the first two cycles comprise a spinner inlet flow rate of 80 mL/min, a reduction spinner revolution rate of 4000 rpm, a desired spinner inlet PCV of 6%, and reduction retentate pump rate of 8 mL/min. The third cycle may be set to a spinner inlet flow rate of 148 mL/min, a reduction spinner revolution rate of 2750 rpm, a desired spinner inlet PCV of 7%, and reduction retentate pump rate of 16 mL/min.

Referring to FIG. 1 and FIG. 4, in one embodiment, apparatus 200 and circuit 100 may be used to process cell products, e.g., leukapheresis products, in preparation for selection of desired WBCs, e.g., surface antigen expressing T-cells.

Figure 6A:
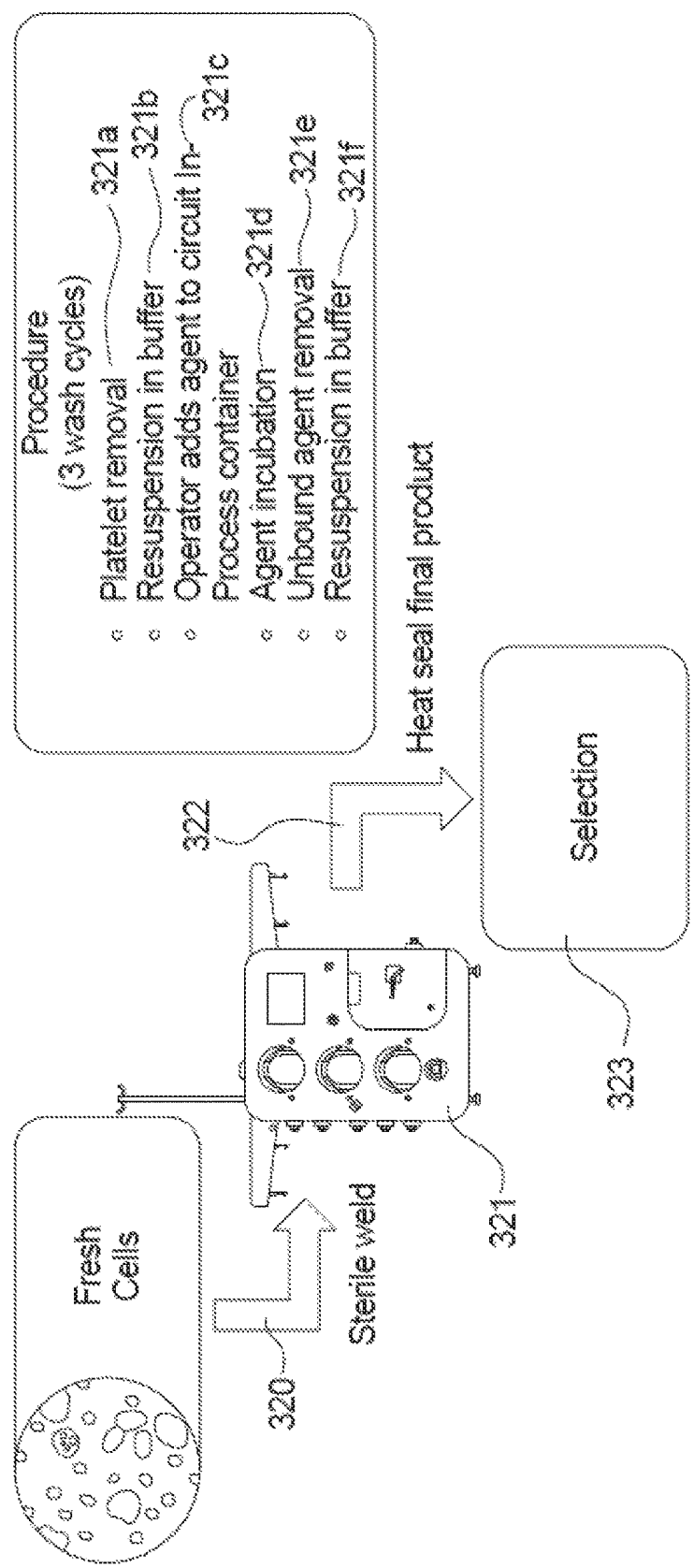
FIG. 6A is a flow diagram illustrating the steps in processing biological cells and performing target cell selection, according to an exemplary embodiment.

Turning to FIG. 6A, a flow diagram is shown, illustrating the steps in processing biological cells and performing target cell selection, according to an exemplary embodiment. At step 320, a sterile circuit 100 may be mounted onto the apparatus 200 (FIG. 4). Source container 102 holding fresh cell product, such as a leukapheresis product (e.g., overnight refrigerated, recently obtained via apheresis, etc.), may be sterile-connected to docking site 104 connected to tubing 106. The cell product may comprise leukocytes, e.g., desired T-cells, suspended in a cell additive solution. Also included within the cell product may be platelets suspended alongside the cells. After apparatus 200 determines that the disposable set 100 is properly installed, the controller may prompt the operator to connect a wash medium. Wash container 135*a* holding the wash medium may be accessed by spike connector 134*a* of the circuit 100. The wash medium may comprise a buffer comprising PBS, EDTA, HSA, and/or saline, although any suitable wash medium may be used.

After the source of biological fluid and wash media have been connected to the disposable set, the fluid circuit 100 may commence the procedure at step 321 comprising platelet removal, resuspension in wash media, agent incubation, excess agent removal, and resuspension in wash media. The fluid circuit 100 may first be primed for the wash process. The circuit 100 may be primed with the wash medium in container 135a or be primed with saline or any other bio-compatible aqueous solution in container 135b, The controller of apparatus 200 may then commence a first cycle comprising a wash. At step 321a, the cell product in container 102 to be washed may be transferred from source container 102 to the spinning membrane separator 101 via the operation of one or more peristaltic pumps 202, 204 and 206. At approximately the same time, the wash medium in container 135a may be delivered through the circuit 100 to the separator 101. The separator 101 may separate the cell product into target cells and remaining supernatant. As stated in Example A, the membrane of the separator 101 may comprise pores having sizes allowing platelets to pass through but not certain cellular components. The target cells may exit the separator 101 through outlet orifice 48 and be directed to the in-process container 122, while the supernatant and formed elements, e.g., platelets, may exit the separator 101 through outlet orifice 46 and be directed to the waste/filtrate bag 140. The supernatant collected in waste/filtrate bag 140 may comprise the cell additive solution and platelets. Wash medium, e.g., buffer comprising PBS, EDTA, HSA, and/or saline, contained in wash container 135a, may then be pumped through the separator 101 to recover any target cells and/or supernatant remaining in the circuit 100 and respectively direct them to the in-process container 122 and/or waste/filtrate bag 140. The contents of the in-process container 122 may comprise concentrated target cells suspended in wash media. In one embodiment, an operator may manually mix the target cells suspended in wash media in the in-process container 122 by holding container 122 with both hands and mixing thoroughly by using a gentle rotating motion, although any suitable mixing method may be used.

At step 321b of FIG. 6A, a second cycle of the procedure may commence, wherein the contents of the in-process container 122 may be diluted further with wash medium in container 135a or 135b in preparation for another pass through the separator 101. The diluted target cells suspended in wash media in container 122 to be washed and concentrated may be transferred from source container 122 to the spinning membrane separator 101 via the operation of one or more peristaltic pumps 202, 204 and 206. The separator 101 may separate the diluted target cells suspended in wash media into target cells and remaining supernatant. The target cells may exit the separator 101 through outlet orifice 48 and be directed again to the in-process container 122, while the supernatant may exit the separator 101 through outlet orifice 46 and be again be directed to the waste/filtrate bag 140. The supernatant collected in waste/filtrate bag 140 may comprise cell additive solution, wash media, and platelets. Wash media, e,g., buffer comprising PBS, EDTA, HSA, and/or saline, contained in wash container 135a or 135b, may then be pumped through the separator 101 to rinse any target cells and/or supernatant remaining in the circuit 100 and respectively direct them to the in-process container 122 and/or waste/filtrate bag 140. The contents of the in-process container 122 may comprise concentrated target cells suspended in wash media.

At step 321c, the reusable hardware apparatus 200 and its controller may be configured to pause automatically after the second cycle at 321b. The pause may allow an operator to inject an incubation agent into the in-process container 122. The incubation agent may be housed in an introducer container 122b (FIG. 1) and sterile-connected to a port 122a of container 122. The introducer container may be pre-attached to the disposable circuit 100 prior to a procedure or may be attached in a sterile manner to container 122 during a procedure. After injection of the incubation agent into container 122, an operator may manually mix the target cells and incubation agent suspended in wash media in the in-process container 122 by holding container 122 with both hands and mixing thoroughly by using a gentle rotating motion, although any suitable mixing method may be used.

At step 321d the agent/target cell conjugated complex, e.g., antibody-conjugated agent, may be incubated during an incubation cycle with the target cells within the in-process container 122 for a suitable period of time, e.g., thirty minutes, at a suitable temperature, e.g., room temperature. In one embodiment, the target cell/agent mixture may be incubated stilly with minimal shaking and/or agitation. In another embodiment, an operator may manually mix the target cell/agent mixture with both hands off the apparatus 200. In another embodiment, apparatus 200 and its controller may allow for an automated incubation cycle comprising gentle mixing achieved by cycling the target cell/agent mixture from the in-process container 122 through tubing 120 to the inlet port 20 of the spinner 101. From spinner 101, the target cell/agent mixture may exit the spinner 101 through outlet port 48, through tubing 168, and back into the in-process container 122. The target cell/agent mixture may be restricted to this cyclical pathway by clamping tubing 138 leading from the outlet port 46 of spinner 101 and also by clamping the flow path leading from branch connector 144 to the product/retentate container 150. During the automated incubation cycle, the flow rate along the cyclical pathway may be set at a suitable rate, according to the specific selection system. The revolution rate of the spinner 101 during the automated incubation cycle may likewise be set at a suitable rate, e.g., 500-700 rpm, appropriate for a particular selection system. During the automated incubation cycle, incubation volume and/or concentration within the product/retentate container 150 may be increased by pumping additional solution(s) and/or agent at a configurable rate into the cycle via e.g., container 135a and/or 135b, Multiple incubation cycles may be implemented with the inclusion of additional pauses and additional sterile connections with the in-process container 122.

Upon completion of the incubation, step 321e comprising a third cycle for unbound agent removal may commence. Wash media within container 135a or 135b may be delivered through the circuit 100 through the separator 101 into in-process container 122 to dilute the incubated target cells resulting from the incubation. An operator may manually mix the diluted incubated target cells in the in-process container 122 by holding container 122 with both hands and mixing thoroughly by using a gentle rotating motion, although any suitable mixing method may be used. The contents of container 122 comprising incubated target cells may then enter the separator 101, which may separate the incubated target cell product into incubated target cells and remaining supernatant. The membrane of the separator 101 may have pores having sizes greater than the diameter of unbound agent and any remaining platelets but less than the diameter of certain cellular components, thereby allowing unbound agent and any remaining platelets to pass through, while not allowing the target cellular components and target cellular components bound to the agent to pass through. The incubated target cells may exit the separator 101 through outlet orifice 48 and be directed to the product/retentate container 150, while the supernatant may exit the separator 101 through outlet orifice 46 and be directed to the waste/ filtrate bag 140. The supernatant collected in waste/filtrate bag 140 may comprise wash media, any remaining platelets, and unbound agent. At step 321f, additional wash media, e.g., buffer comprising PBS, EDTA, HSA, and/or saline, contained in wash container 135a or 135b, may then be pumped through the separator 101 to recover any incubated target cells and/or supernatant remaining in the circuit 100 and respectively direct them to the product/retentate container 150 and/or waste/filtrate bag 140. The contents of the product/retentate container 150 containing incubated target cells may comprise, e.g., desired T-cells bound to the agent, and e.g., undesired T-cells not bound to the agent, suspended in wash media.

After completion of the third cycle, the product/retentate container 150 may be disconnected at step 322 of FIG. 6A from the remainder of the circuit 100 and from the apparatus 200 in a sterile manner, e.g., heat-seal. At step 323, an operator may subject the incubated target cells, e.g., target leukocytes, within container 150 to a cell selection system to separate the target surface antigen expressing WBCs bound to the agent from the cells not presenting the target antigen, i.e., not bound to the agent, as described in Example A.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Other Aspects

Aspect 1. A system for automated processing of a cell product comprising surface antigen expressing cells, in preparation for surface antigen expressing cell selection, the system comprising:
  a reusable separation apparatus controlled by a microprocessing controller unit driven by software, wherein the apparatus and microprocessing controller unit are configurable with a plurality of settings;
  a disposable sterile circuit configured to associate with the reusable separation apparatus, the disposable sterile circuit comprising a spinning membrane separator comprising a porous membrane, wherein the separator comprises an inlet and first and second outlets;
  a cell product in communication with the inlet of the separator, wherein the separation apparatus is configured in a first cycle by the microprocessing controller to flow the cell product into the inlet of the separator, separate platelets and supernatant from the first outlet into a filtrate container, and separate remaining cellular components from the second outlet into an in-process container;
  wash media within a media container in communication with the in-process container wherein the separator is configured by the separation apparatus in a second cycle to flow the wash media into the in-process container containing the remaining cellular components to form resuspended platelet-depleted cell product;
  a port located on the in-process container configured to receive an agent having an association with the surface antigen expressing cells of the resuspended platelet-depleted cell product, wherein the in-process container is configured to incubate the agent with the surface antigen expressing cells over an incubation period sufficient for the agent to bind and/or associate with the surface antigen expressing cells to form a first mixture, comprising antigen-agent complexes, unbound/unassociated agent, and cells not presenting the antigen;
  wherein the separation apparatus is configured in a third cycle to separate the first mixture into unbound/unassociated agent, directed from the first outlet into the filtrate container, and a second mixture, comprising antigen-agent complexes and cells not expressing the antigen, directed from the second outlet to a retentate container, wherein the second mixture is ready for target cell selection.

Aspect 2. The system of aspect 1, wherein the plurality of settings further comprises:
  a spinner inlet flow rate of 80 mL/min, a reduction spinner evolution rate of 4000 rpm, a desired spinner inlet PCV of 6%, and a reduction retentate pump rate of 8 mL/min for the first cycle and the second cycle; and
  a spinner inlet flow rate of 148 mL/min, a reduction spinner revolution rate of 2750 rpm, a desired spinner inlet PCV of 7%, and reduction retentate pump rate of 16 mL/min for the third cycle.

Aspect 3. The system of aspect 1 or 2, wherein the wash media comprises at least one of PBS, EDTA, HSA, and saline.

Aspect 4. The system of any one of the preceding aspects, wherein the porous membrane comprises pore sizes greater than the size of platelets and the unbound/unassociated agent but less than the size of the cellular components.

Aspect 5. The system of aspect 4, wherein the pore sizes are within the range of 4.0 μm to 10.0 μm.

Aspect 6. The system of any one of the preceding aspects, wherein the reusable separation apparatus controlled by a microprocessing controller unit is configured to automatically pause between the first cycle and the second cycle, and/or a beginning of the incubation period and the third cycle, to allow an operator may manually mix the in-process container.

Aspect 7. The system of any one of the preceding aspects, wherein the incubation period further comprises an automated incubation cycle, wherein the separation apparatus controlled by the microprocessing unit is configured to cycle the agent and the resuspended platelet-depleted cell product from the in-process container through the separator and back to the in-process container in a cyclical pathway.

Aspect 8. The system of any one of the preceding aspects, wherein during the incubation period, the separation apparatus controlled by the microprocessing unit is configured to add additional volume of fluid and/or substrate gradually and/or intermittently, via a second media container in communication with the in-process container, to the resuspended platelet-depleted cell product.

Aspect 9. A method for automated processing of a leukapheresis product comprising surface antigen expressing cells, in preparation for surface antigen expressing cell selection, the method comprising:
  providing a reusable separation apparatus controlled by a microprocessing unit driven by software, said apparatus configurable with a plurality of settings and configured to associate with a disposable sterile circuit comprising a separator comprising a porous membrane and in communication with the leukapheresis product, wherein the apparatus and disposable sterile circuit are configured to:
    remove platelets from the leukapheresis product in a first cycle to form a platelet-depleted leukapheresis product;

resuspend the platelet-depleted leukapheresis product in media in a second cycle to form a resuspended platelet-depleted leukapheresis product;

receive an agent having an association with the surface antigen expressing cells of the resuspended platelet-depleted leukapheresis product;

incubate the agent with the surface antigen expressing cells over an incubation period sufficient for the agent to bind/associate with the surface antigen expressing cells to form a first mixture comprising antigen-agent complexes, unbound/unassociated agent, and cells not presenting the antigen; and remove unbound/unassociated agent in a third cycle to form a second mixture ready for target cell selection, wherein the second mixture comprises the antigen-agent complexes and cells not presenting the antigen.

Aspect 10. The method of aspect 9, wherein the plurality of settings further comprises:

a spinner inlet flow rate of 80 mL/min, a reduction spinner evolution rate of 4000 rpm, a desired spinner inlet PCV of 6%, and a reduction retentate pump rate of 8 mL/min for the first cycle and the second cycle; and a spinner inlet flow rate of 148 mL/min, a reduction spinner revolution rate of 2750 rpm, a desired spinner inlet PCV of 7%, and reduction retentate pump rate of 16 mL/min for the third cycle.

Aspect 11. The method of aspect 9 or 10, wherein the media comprises at least one of PBS, EDTA, HSA, and saline.

Aspect 12. The method of any one of aspects 9-11, wherein the porous membrane comprises pore sizes greater than the size of platelets and unbound/unassociated agent but less than the size of cellular components.

Aspect 13. The method of aspect 12, wherein the pore sizes are within the range of 4.0 μm to 10.0 μm.

Aspect 14. The method of any one of aspects 9-13, wherein the reusable separation apparatus controlled by a microprocessing controller unit is configured to automatically pause between the first cycle and the second cycle, and/or a beginning of the incubation period and the third cycle, to allow an operator to manually mix the platelet-depleted leukapheresis product, and/or the first mixture, respectively.

Aspect 15. The method of any one of aspects 9-14, wherein the incubation period further comprises an automated incubation cycle, wherein the separation apparatus controlled by the microprocessing unit is configured to cycle the agent and the resuspended platelet-depleted leukapheresis product through the separator within the disposable circuit in a cyclical pathway.

Aspect 16. The method of any one of aspects 9-15, wherein during the incubation period, the separation apparatus controlled by the microprocessing unit is configured to add additional volume of fluid and/or substrate gradually and/or intermittently to the resuspended platelet-depleted leukapheresis product.

Aspect 17. The method of any one of aspects 9-16, wherein the second cycle further comprises collecting the resuspended platelet-depleted leukapheresis product in a first retentate container and removing the first retentate container from the sterile circuit, wherein the first retentate container is configured to receive the agent within an enclosed, ventilated laboratory workspace, wherein the agent is incubated on a shaker with the surface antigen expressing cells over the incubation period to form the first mixture; and wherein the third cycle further comprises removing the unbound/unassociated agent from the first mixture of the first retentate container sterile-connected to be in communication with an inlet of the separator, to form the second mixture ready for target cell selection, wherein the second mixture is collected in a second retentate container sterile-connected to the sterile circuit.

Aspect 18. The method of aspect 17, wherein the plurality of settings comprises:

a spinner inlet flow rate of 150 mL/min, a reduction spinner revolution rate of 3750 rpm, a desired spinner inlet PCV of 3%, and a reduction retentate pump rate of 15 mL/min for the first, second, and third cycles; or a spinner inlet flow rate of 80 mL/min, a reduction spinner revolution rate of 4000 rpm, a desired spinner inlet PCV of 6%, and reduction retentate pump rate of 8 mL/min for the first, second, and third cycles.

Aspect 19. A method for automated processing of a cellular product comprising target substrate cells, in preparation for target cell selection, the method comprising:

providing a reusable separation apparatus controlled by a microprocessing unit driven by software, said apparatus configurable with a plurality of settings and configured to associate with a disposable sterile circuit comprising a separator comprising a porous membrane and in communication with the cellular product, wherein the apparatus and disposable sterile circuit are configured to:

remove platelets from the cellular product in a first cycle to form a platelet-depleted cellular product;

resuspend the platelet-depleted cellular product in media in a second cycle to form a resuspended platelet-depleted cellular product;

receive an agent having an association with the target substrate cells of the resuspended platelet-depleted cellular product;

incubate the agent with the target substrate cells over an incubation period sufficient for the agent to bind with and/or enter the target substrate cells to form a first mixture comprising agent-target substrate cell complexes, unbound/unassociated agent, and non-target substrate cells; and remove unbound/unassociated agent in a third cycle to form a second mixture ready for target cell selection, wherein the second mixture comprises the agent-target substrate cell complexes and non-target substrate cells.

Aspect 20. The method of aspect 19, wherein the incubation period further comprises an automated incubation cycle, wherein the separation apparatus controlled by the microprocessing unit is configured to cycle the agent and the resuspended platelet-depleted cellular product through the separator within the disposable circuit in a cyclical pathway.

The invention claimed is:

1. A system for automated processing of a cell product comprising surface antigen expressing cells, in preparation for surface antigen expressing cell selection, the system comprising:

a reusable separation apparatus controlled by a microprocessing controller unit driven by software, wherein the apparatus and microprocessing controller unit are configurable with a plurality of settings;

a disposable sterile circuit configured to associate with the reusable separation apparatus, the disposable sterile circuit comprising a spinning membrane separator comprising a porous membrane, wherein the separator comprises an inlet and first and second outlets;

a cell product in communication with the inlet of the separator, wherein the separation apparatus is configured in a first cycle by the microprocessing controller unit to flow the cell product into the inlet of the separator, separate platelets and supernatant from the first outlet into a filtrate container, and separate remaining cellular components from the second outlet into an in-process container;

wash media within a media container in communication with the in-process container, wherein the separator is configured by the separation apparatus in a second cycle to flow the wash media into the in-process container containing the remaining cellular components to form resuspended platelet-depleted cell product;

an external injection port located on the in-process container configured to receive an agent having an association with the surface antigen expressing cells of the resuspended platelet-depleted cell product, wherein the in-process container is configured to incubate the agent with the surface antigen expressing cells over an incubation period sufficient for the agent to bind and/or associate with the surface antigen expressing cells to form a first mixture, comprising antigen-agent complexes, unbound/unassociated agent, and cells not presenting the antigen;

wherein the separation apparatus is configured in a third cycle to separate the first mixture into unbound/unassociated agent, directed from the first outlet into the filtrate container, and a second mixture, comprising antigen-agent complexes and cells not expressing the antigen, directed from the second outlet to a retentate container, wherein the second mixture is ready for target cell selection.

2. The system of claim 1, wherein the plurality of settings further comprises:
a spinner inlet flow rate of 80 mL/min, a reduction spinner revolution rate of 4000 rpm, a desired spinner inlet packed cell volume (PCV) of 6%, and a reduction retentate pump rate of 8 mL/min for the first cycle and the second cycle; and
a spinner inlet flow rate of 148 mL/min, a reduction spinner revolution rate of 2750 rpm, a desired spinner inlet packed cell volume (PCV) of 7%, and reduction retentate pump rate of 16 mL/min for the third cycle.

3. The system of claim 1, wherein the wash media comprises at least one of Phosphate-Buffered Saline (PBS), Ethylenediaminetetraacetic Acid (EDTA), Human Serum Albumin (HAS), and saline.

4. The system of claim 1, wherein the porous membrane comprises pore sizes greater than the size of platelets and the unbound/unassociated agent but less than the size of the cellular components.

5. The system of claim 4, wherein the pore sizes are within the range of 4.0 μm to 10.0 μm.

6. The system of claim 1, wherein the reusable separation apparatus controlled by a microprocessing controller unit is configured to automatically pause between the first cycle and the second cycle, and/or a beginning of the incubation period and the third cycle, to allow an operator may manually mix the in-process container.

7. The system of claim 1, wherein the incubation period further comprises an automated incubation cycle, wherein the separation apparatus controlled by the microprocessing controller unit is configured to cycle the agent and the resuspended platelet-depleted cell product from the in-process container through the separator and back to the in-process container in a cyclical pathway.

8. The system of claim 1, wherein during the incubation period, the separation apparatus controlled by the microprocessing controller unit is configured to add additional volume of fluid and/or substrate gradually and/or intermittently, via a second media container in communication with the in-process container, to the resuspended platelet-depleted cell product.

9. The system of claim 1, wherein the in-process container is configured to receive the agent within an enclosed, ventilated laboratory workspace, wherein the agent is incubated on a shaker with the surface antigen expressing cells over the incubation period to form the first mixture.

10. The system of claim 1, wherein the plurality of settings comprises:
a spinner inlet flow rate of 150 mL/min, a reduction spinner revolution rate of 3750 rpm, a desired spinner inlet packed cell volume (PCV) of 3%, and a reduction retentate pump rate of 15 mL/min for the first, second, and third cycles; or
a spinner inlet flow rate of 80 mL/min, a reduction spinner revolution rate of 4000 rpm, a desired spinner inlet packed cell volume (PCV) of 6%, and reduction retentate pump rate of 8 mL/min for the first, second, and third cycles.

* * * * *